United States Patent [19]

Yang et al.

[11] Patent Number: 4,497,958
[45] Date of Patent: Feb. 5, 1985

[54] PROCESS FOR OXIDIZING A CARBOXYLIC ANHYDRIDE WITH HETEROGENEOUSLY PREPARED VANADIUM-PHOSPHORUS-OXYGEN CONTAINING CATALYST COMPOSITION

[75] Inventors: Tai-Cheng Yang, Mahwah; Krishna K. Rao, Paterson; I-der Huang, Upper Saddle River, all of N.J.

[73] Assignee: Exxon Research & Engineering Co., Florham Park, N.Y.

[21] Appl. No.: 538,119

[22] Filed: Oct. 3, 1983

Related U.S. Application Data

[62] Division of Ser. No. 381,206, May 24, 1982, Pat. No. 4,439,921.

[51] Int. Cl.³ .................. C07D 307/60; C07D 307/89; C07D 307/92

[52] U.S. Cl. .................................. 549/239; 549/245; 549/248; 549/253; 549/256; 549/257; 549/250; 549/260

[58] Field of Search ............... 549/239, 245, 248, 253, 549/256, 257, 259, 260

[56] References Cited

U.S. PATENT DOCUMENTS 4,400,522 8/1983 Lemanski et al. ................... 549/260
4,429,137 1/1984 Blum et al. ..................... 549/260 X Primary Examiner—Richard Raymond
Attorney, Agent, or Firm—Robert A. Maggio

[57] ABSTRACT

A heterogeneous process for preparing a vanadium-phosphorus-oxygen containing catalyst for use in the preparation of carboxylic anhydrides is disclosed. This process employs an activation procedure in an air-hydrocarbon atmosphere.

3 Claims, No Drawings

PROCESS FOR OXIDIZING A CARBOXYLIC ANHYDRIDE WITH HETEROGENEOUSLY PREPARED VANADIUM-PHOSPHORUS-OXYGEN CONTAINING CATALYST COMPOSITION

This is a division, of application Ser. No. 381,206, filed May 24, 1982, now U.S. Pat. No. 4,439,521.

BACKGROUND OF THE INVENTION

This invention relates to an improved process for preparing oxidation catalysts, and its use in a process for the preparation of carboxylic acid anhydrides from hydrocarbons. More particularly, it relates to a novel and simpler method for the production of vanadium-phosphorus-oxygen catalyst composites by a heterogeneous solution reducing method providing increased yields. Still more particularly, it relates to the production of maleic anhydride from n-butane, or n-butene, in a vapor phase process employing catalyst prepared by the process of the present invention.

Methods for the preparation of catalyst compositions of vanadium, phosphorus, and oxygen, and the use of these compositions as catalysts in hydrocarbon oxidations are known in the art.

Such preparative methods can be generally categorized as being aqueous-based or organic-based and employ either homogeneous solutions and/or heterogeneous mixtures (e.g., suspensions) of at least one of the components (e.g., a vanadium containing compound) which eventually forms the catalyst composition.

The particular method of preparation selected will depend on the various combination of properties sought to be imparted to the catalyst and the commercial attractiveness of the process. Particularly significant properties sought to be influenced by the catalyst preparative methods of the prior art include the vanadium valence, the P:V atomic ratio, the crystal phases of the catalyst, and the surface area of the catalyst.

While at least one patent seeks to impart a vanadium valence of less than +3.9, namely, U.S. Pat. No. 4,178,298, a majority of patents seek to obtain a vanadium valence between +4 and +5.

One preferred way of achieving this is to begin with vanadium in the +5 valence state and reduce the valency to less than +5, or alternatively to start with a vanadium compound having a valency of less than +5. A wide variety of reducing agents can be employed for the former reducing method approach. Representative of such reducing agents include acids such as hydrochloric, hydroiodic, hydrobromic, acetic, oxalic, malic, citric, formic and mixtures thereof such as a mixture of hydrochloric and oxalic may be used. Sulphur dioxide may be used. Less desirably, sulfuric and hydrofluoric acids may be employed. Other reducing agents which may be employed are organic aldehydes such as formaldehyde and acetaldehyde; alcohols such as pentaerythritol, diacetone alcohol and diethanol amine. Additional reducing agents include hydroxyl amines, hydrazine, nitric acid, and the like.

Reducing methods also can be classified according to whether the vanadium compound is dissolved, e.g., solution reducing methods, or not, e.g., heterogeneous reducing methods.

In accordance with solution reducing methods, a vanadium compound having a valence of +5 such as $V_2O_5$ is dissolved in a solution containing the reducing agent. Because many strong acid reducing agents, such as HCl, also function to dissolve the vanadium compound, and, therefore, act as a solvent, the solvent and reducing agent can be the same (see for example Kerr, U.S. Pat. No. 3,288,721). Thus, a strong acid reducing agent (e.g., HCl) can be employed in an aqueous or non-aqueous (e.g., organic) medium to achieve dissolution and reduction therein. The phosphorus compound can be added to the vanadium compound for reaction therewith before or after vanadium reduction takes place to form the V-P-O catalyst precursor.

After the aforedescribed reducing methods are employed and the V-P-O catalyst precursor is formed, it is conventional to subject the resulting precursor to some type of activation procedure. The particular set of activation conditions which are employed depends on the initial treatment procedures employed in the preparation of the precursor to be activated.

Thus, it is conventional to activate vanadium-phosphorus-oxygen containing compositions prepared by the aqueous-based solution reduction method by contacting the same with a reducing atmosphere such as CO, $H_2$, $H_2S$ and in the essential absence of added gaseous oxygen at temperatures of about 300° to 600° C. (see for example U.S. Pat. Nos. 4,062,802 and 4,122,096). Other activation methods applied to compositions prepared by aqueous-based solution reduction methods include: calcining in an inert atmosphere such as $CO_2$, $N_2$, a noble gas, or butane free oxygen (U.S. Pat. Nos. 3,907,707, and/or 4,178,298, and/or 4,111,963); calcining in oxygen (e.g., air) and then an inert atmosphere, e.g., $N_2$ or noble gas, (U.S. Pat. No. 3,977,998); calcining in air or an oxidizing gas alone (U.S. Pat. Nos. 3,907,707 and 4,111,963 where P:V atomic ratio is greater than 1:1; 3,915,892; and 4,179,404); and heating in a gaseous mixture containing air and a reducing component, e.g., butane (U.S. Pat. No. 3,915,892).

Activation methods for vanadium-phosphorus-oxygen containing compositions prepared by organic-based solution reduction methods can be conducted by heating in air alone and then a gaseous mixture of air and butane. An illustration of this type of activation procedure is found in U.S. Pat. Nos. 3,864,280 and 4,017,521. Activation in air alone is disclosed in U.S. Pat. No. 4,179,404. U.S. Pat. No. 4,043,943 discloses an organic-based solution reduction method wherein a vanadium phosphate compound is precipitated from a liquid organic medium and activated. While it is broadly disclosed (col.10, lines 16 to 23) that the average vanadium valence can be varied somewhat by oxidative or reductive treatment after precipitation as by subjecting the precipitated solid to an oxidizing or reducing atmosphere, these treatments are a less preferred substitution for the use of a suitable oxidizing or reducing reagent to impart a vanadium valence of 3.8 to 4.6, and do not constitute or perform the function of activation. The activation procedure is described at col.2, lines 59–62, i.e., calcination at a temperature of 100° to 500° C., and at col.12, lines 29 to 32, i.e., in an atmosphere of air alone and then a mixture of air and butane.

Thus, none of the prior art appears to be directed to preparing a V-P-O containing composition by an organic-based solution reduction method followed by activation in an atmosphere which excludes air alone at any time during the activation procedure.

Similar observations can be made with respect to conventional organic-based heterogeneous reduction methods. Organic-based heterogeneous reduction methods can be classified into those which reduce the vanadium compound in an organic slurry prior to or after contact with the phosphorus compound. For example, U.S. Pat. Nos. 4,132,670 and 4,187,235, which both contain essentially the same disclosure, are directed to an organic-based heterogeneous suspension type reduction method wherein $V_2O_5$ is first reduced with a suitable liquid organic medium, e.g., isobutanol, to impart a vanadium valence of between 4.0 and 4.6, and subsequently contacting the reduced vanadium compound with, for example, orthophosphoric acid to form a heterogeneous slurried reaction mixture of a suspended vanadium (IV) phosphate composition. This composition is recovered and calcined, i.e., activated, at about 380° C. by contact with a stream of air alone, and then a gaseous mixture of air and butane. The performance of the catalyst is disclosed as being severely dependent on this activation procedure (col. 7, lines 55–61 of U.S. Pat. No. 4,132,670). The present invention is directed to an improvement in this process.

European Patent Application Publication No. 0039 537, published Nov. 11, 1981 and based on U.S. patent application Ser. No. 146,971 filed May 5, 1980 discloses an organic heterogeneous slurry reducing method wherein a pentavalent vanadium compound and phosphorus compound are admixed prior to reducing the vanadium valence with, for example, isobutanol. The resulting catalyst precursor is calcined in air or an oxygen containing gas at a temperature of 250° to 600° C. Not only does this application fail to disclose the advantage of excluding air alone as an activation or calcination atmosphere, but as described in Comparative Example 2, the catalyst of this application performs better when activated in air alone relative to the exclusion of air alone in favor of an air and butane mixture.

U.S. Pat. No. 4,317,778 discloses a variety of V-P-O catalyst preparative methods, including aqueous and organic, solution and heterogeneous, reduction methods, all of which require the use of specific ratios of orthophosphoric and pyrophosphoric acids as the source of the phosphorus compound to minimize the solubility of the catalyst in water and thereby to enable the catalyst to be spray dried. The catalyst precursor is calcined in air or an oxygen containing gas at temperatures of 250° to 600° C. The catalyst precursor may also be calcined "either in the presence of hydrocarbon, in an inert gas, or both," (col.6, lines 50 et seq.). This patent, however, does not disclose the particular combination of catalyst precursor preparative method and activation procedure of the present invention.

U.S. Pat. No. 3,985,775 discloses organic and aqueous solution reduction methods using HCl, as well as an organic heterogeneous method wherein vanadium is reduced and reacted with a phosphorus containing compound while the vanadium compound is suspended in an organic solvent (e.g., THF, example 14) to form a dihydrate precursor. However, it is suggested therein that even when employing an organic-based method, as much as 20 to 40% by weight of the liquid medium can be water (col.6, lines 21–23). Furthermore, while several general classes of liquid organic media are disclosed, i.e., alcohols, ethers, and carboxylic acids, no preference for alcohols is expressed, nor is there any exemplification of the use of any alcohol in any organic based procedure. Numerous, i.e., eight, different complicated activation, i.e., pretreatment procedures are also disclosed, only one of which avoids contact of the dihydrate with air alone, namely, pretreatment method H. However, pretreatment method H is only applied to an aqueous-based solution reduced dihydrate composition. The pretreatment procedure applied by exemplification to an organic-based heterogeneously reduced dihydrate, employs contact with air alone and then air and butane (example 14). Moreover, the results obtained using pretreatment H are inferior to a majority of the other pretreatment methods, and these results are reported after 530 hours run time, more than twice the run time of any other catalyst prepared by other pretreatment methods. Thus, this reference provides no suggestion of selecting the operative preparative variables to include an alcohol as the liquid medium, a heterogeneous treatment of vanadium to reduce the vanadium in the absence of a phosphorus compound, reaction of the reduced vanadium compound with a phosphorus compound in a heterogeneous reaction mixture, and activation of the resulting product in a hydrocarbon-air atmosphere.

U.S. Pat. No. 3,975,300 is directed to a one-step method for preparing vanadium-phosphorus composites wherein a paste comprising an organic reducing agent, e.g., ethylene glycol, phosphoric acid, and a vanadium compound is formed and then evaporated to dryness. The dried composition is then optionally conditioned in a hydrocarbon-air mixture at about 450° C. This process differs from the process of U.S. Pat. No. 4,132,670 in that reduction of vanadium takes place in the presence of phosphoric acid and a slurry or suspension of the components of the paste is never prepared.

SUMMARY OF THE INVENTION

In one aspect of the present invention there is provided a process for preparing a catalyst composition comprising vanadium, phosphorus and oxygen capable of catalyzing the oxidation of hydrocarbons which comprises:

(a) admixing to form a heterogeneous suspension at least one pentavalent vanadium compound with at least one organic alcohol in a manner and under conditions sufficient to condition said vanadium compound and reduce at least a portion of the pentavalent vanadium to a +4 valence state;

(b) admixing at least one organic alcohol, said conditioned vanadium compound, and at least one phosphorus containing compound, in a manner and under conditions sufficient to form a heterogeneous suspension of a vanadium-phosphorus-oxygen containing catalyst precursor composition having a vanadium valence of from about 3.9 to about 4.7, and a phosphorus to vanadium atomic ratio of from about 0.5:1 to about 2:1;

(c) separating said catalyst precursor composition from said admixture; and (d) activating said catalyst precursor composition by contacting it with an atmosphere comprising a mixture of air and at least one hydrocarbon.

In another aspect of the present invention there is provided a process for oxidizing feed hydrocarbons using a catalyst prepared by the above described process.

DESCRIPTION OF PREFERRED EMBODIMENTS

The present invention is directed to an organic heterogeneous suspension method for preparing a vanadium-phosphorus-oxygen containing catalyst which employs an activation procedure in a butane-air atmosphere at elevated temperatures. In addition to improving the performance of the catalyst vis-a-vis the oxidation of hydrocarbons, the process of the present invention is simple to carry out and requires a much less time consuming activation procedure.

I. PREPARATION OF CATALYST PRECURSOR

In accordance with the first step of the process of the present invention, a pentavalent vanadium compound is treated with at least one organic alcohol to at least partially reduce and condition it for reaction with a phosphorus compound. It is believed that this reduction and conditioning occurs through the formation of vanadyl alkoxides by reaction of the pentavalent vanadium compound with the organic alcohol. The vanadyl alkoxides then react with the phosphorus compound when added producing water as a by-product.

The vanadium reduction step is conducted by heating in the absence of a phosphorus containing compound, a first reaction mixture comprising a pentavalent vanadium compound and at least one organic alcohol under conditions and in a manner sufficient to reduce at least a portion of the pentavalent vanadium to the $+4$ valence state. This will permit the subsequent formation of the vanadium phosphorus oxygen precursor composition having an average vanadium valence as described hereinafter.

Suitable vanadium compounds containing pentavalent vanadium include: vanadium pentoxide or vanadium salts, such as ammonium metavanadate and vanadium oxytrihalides. Vanadium pentoxide is preferred.

"Organic alcohol" is defined herein to be one which is represented by the structural formula:

R—(OH)$_n$ wherein R represents a hydrocarbyl group selected from alkyl, typically about $C_1$ to about $C_{20}$, preferably about $C_1$ to about $C_{10}$, most preferably about $C_1$ to about $C_5$ alkyl; aryl, typically about $C_6$ to about $C_{14}$, preferably about $C_6$ to about $C_{10}$, most preferably $C_6$ aryl, cycloalkyl, typically about $C_4$ to about $C_{20}$, preferably about $C_6$ to about $C_{12}$, most preferably about $C_6$ to $C_{10}$ cycloalkyl, aralkyl and alkaryl wherein the alkyl and aryl groups thereof are described above.

The preferred organic alcohols are the primary and secondary alcohols. Alcohols which contain 1, 2 or 3 hydroxyl substituent groups are especially preferred because these, in general, are readily liquified at useful temperatures in the process range. Representative organic alcohols useful in the process include monoalcohols, such as methanol, ethanol, isopropanol, 1-propanol, 2-propanol, 1-butanol, isobutanol, 2-butanol, tertiary butyl alcohol, 1-pentanol, cyclohexanol, 1-octanol, 2-octanol, 3-octanol, 4-octanol, 2-hexadecanol, 2-eicosanol, 2-ethyl-1-hexanol, benzyl alcohol, etc.; di-alcohols, such as ethylene glycol, 1,4-butanediol, 1,2-propanediol, tri-alcohols such as glycerine, 2,2-dimethylol-1-propanol; ether alcohols such as diethylene glycol, triethylene glycol, 2-butoxy ethanol, 4-methoxybutanol, tetrahydrofurfuryl alcohol; and mixtures thereof.

The primary and secondary alkanols having a carbon atom content in the range from 3 to 6 are a preferred class of organic alcohol for reason of cost and availability and because of their convenient boiling points. Isobutanol is the optimum alcohol.

In the vanadium reduction step the organic alcohol functions as suspending agent for the pentavalent vanadium compound, and as a reactant for the vanadyl alkoxide formation.

More specifically, in conducting the vanadium reduction step, the pentavalent vanadium compound is admixed with a suitable organic alcohol to form a heterogeneous suspension of the vanadium compound, and the suspension is heated to a temperature of typically from about 30° to about 300° C., preferably from about 60° to about 200° C., and most preferably from about 80° to about 150° C. for a period of from about 1 to about 50 hours, preferably from about 2 to about 40 hours, and most preferably from about 3 to about 30 hours. Preferably, the organic alcohol selected will boil at about the selected temperature so the reaction can be conducted by refluxing. Thus, when isobutanol is used as the organic alcohol, simple refluxing at about 108° C. (1 ATM) for a period of from about 5 to about 8 hours will suffice. The reaction mixture is typically maintained in the substantially anhydrous, preferably anhydrous, state by removing any water formed in-situ by azeotropic distillation or other suitable means. By "substantially anhydrous" as used herein is meant typically less than about 10%, preferably less than about 5%, and most preferably less than about 1%, by weight water, based on the weight of the organic alcohol in the reaction mixture. Since the pentavalent vanadium compound is only slightly soluble in the organic alcohol, the reaction mixture will comprise a heterogeneous suspension.

Since the organic alcohol is believed to result in the formation of a vanadyl alkoxide which can be represented by the structural formula:

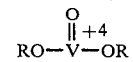

$$\overset{\overset{\displaystyle O}{\|}}{RO-V-OR}\,^{+4}$$

wherein R represents the residual organic moiety contributed by the alcohol, stoichiometric considerations lead to the conclusion that at least 2 moles of organic alcohol per g/atom of vanadium should be employed in the vanadium reduction, e.g., at least 4 moles of alcohol per mole of $V_2O_5$. There is no upper limit on the amount of organic alcohol, and the use of excess alcohol is in fact preferred.

Thus, the organic alcohol is employed in the reaction mixture in amounts effective to provide uniform heating and reaction of the pentavalent vanadium compound, and preferably to provide a slurry or suspension which can be conveniently refluxed at the selected treatment temperature. While any effective amount of organic alcohol can be employed in the vanadium reduction step, such effective amounts typically will constitute from about 50 to about 90%, preferably from about 60 to about 85%, and most preferably from about 70 to about 80%, by weight, based on the combined weight of organic alcohol and vanadium compound.

The pressure at which the vanadium reduction is conducted is not critical, provided the reaction mixture is maintained in the liquid state.

Upon completion of the vanadium reduction step, the reaction mixture is preferably cooled to between about 20° and 50° C. The entire reaction mixture can be employed in the next step, preferably after concentrating the reduced vanadium compound by distillation, or the reduced vanadium compound can be separated from the reaction mixture by filtration, decantation, or other means and used in the next step.

In the second step of the process, the conditioned vanadium compound is reacted with a phosphorus containing compound in the presence of at least one organic alcohol to form a vanadium-phosphorus-oxygen precursor composition having an average vanadium valence of typically between about 3.9 and about 4.7, preferably between about 3.9 and 4.4, most preferably between about 3.9 and 4.1; and a P:V atomic ratio of typically from about 0.5:1 to about 2:1 (e.g., about 0.6:1 to about 2:1) preferably from about 0.9:1 to about 1.5:1, most preferably from about 1:1 to about 1.3:1. Generally the P:V atomic ratio is at least 1:1 and not more than 1.4:1.

The phosphorus containing compound useful as a source of phosphorus in the catalyst precursor is well known in the art. Suitable phosphorus containing compounds include phosphoric acid, such as metaphosphoric acid, orthophosphoric acid, triphosphoric acid and pyrophosphoric acid; phosphorus oxides, such as phosphorus pentoxide; phosphorus halides and oxyhalides, such as phosphorus oxyiodide, phosphorus pentachloride and phosphorus oxybromide; phosphorus salts such as mono-, di-, and tri-ammonium phosphates; and organophosphorus compounds, such as ethyl phosphate and methyl phosphate as well as mixtures thereof.

However, the phosphoric acids, such as orthophosporic acid and pyrophosphoric acid and mixtures thereof are preferred. More specifically, phosphoric acid generally will be employed as an aqueous solution or mixture having a concentration of typically at least 85%, preferably at least 90%, and most preferably at least 95%, by weight, based on the weight of the solution or mixture. However, substantial improvements in the performance of the catalyst can be achieved by employing substantially anhydrous phosphoric acid, e.g., orthophosphoric acid. Polyphosphoric acid is another preferred type of anhydrous phosphoric acid. This acid is commercially available as a mixture of orthophosphoric acid with pyrophosporic, triphosphoric and higher acids, and is sold on the basis of its calculated content of $H_3PO_4$, as for example 115%. Superphosphoric acid is a similar mixture sold at 105% $H_3PO_4$. These acids revert primarily to orthophosphoric acid upon dilution with water.

In the second step of the subject process the organic alcohol functions as a suspending agent for the reduced vanadium compound, as a solvent and/or diluent for the phosphoric acid, and as a suspending agent for the catalyst precursor. Accordingly, the identity of the organic alcohol is selected in accordance with these functions.

The precursor composition is produced by heating, preferably refluxing, a reaction mixture comprising the conditioned vanadium compound, at least one phosphorous compound and at least one organic alcohol at temperatures of typically from about 30° to about 300° C., preferably from about 60° to about 200° C., and most preferably from about 80° to about 150° C., for a period of typically from about 1 to about 50 hours, preferably from about 10 to about 35 hours, and most preferably from about 15 to about 25 hours to form the catalyst precursor. Heating is preferably conducted until the vanadium attains an average vanadium valence of preferably between about 4.0 and about 4.3. Suitable reduction is indicated to have been achieved when the color of the reaction mixture turns blue (e.g., indicative of a valence of between about 4.0 and 4.3). The identity of the liquid organic media is preferably selected to that it will reflux at the selected reaction temperature.

The amounts of reduced vanadium compound and phosphorus compound which are present in the reaction mixture is controlled to achieve, in the precursor composition, a P:V atomic ratio as described above.

The organic alcohol is present in the reaction mixture in an amount effective to reduce the vanadium to achieve the described valence, to suspend it and the resulting catalyst precursor in a slurry, and dilute the phosphorus compound as well as the other components of the reaction mixture to the extent that uniform heating and mixing of the reactants is possible.

The term "slurry" as used in connection with the catalyst precursor forming step wherein the vanadium compound is reacted with the phosphorus compound is defined herein to mean a suspension wherein the solid components thereof are present therein at a solids content of typically not greater than about 50, preferably not greater than about 40, and most preferably not greater than about 25%, by weight, based on the weight of the suspension. Thus, while any effective amount of the organic alcohol can be employed in the reaction mixture, such effective amounts typically will constitute from about 50 to about 98%, preferably from about 60 to about 95%, and most preferably from about 75 to about 90%, by weight, based on the combined weight of the vanadium and phosphorus compounds and the organic alcohol.

The precursor forming reaction is preferably conducted to maintain the reaction mixture in the substantially anhydrous state, most preferably anhydrous state, by for example, azeotropic distillation to remove any water formed in-situ or any other low boiling compounds.

The reaction pressure for the precursor forming reaction is not critical and can be subatmospheric, atmospheric, or superatmospheric provided the reactants and organic alcohol do not volatilize to the extent that the composition of the reaction mixture is altered from the description provided herein. Atmospheric pressure is preferred.

In addition to organic alcohols, the reaction mixture can comprise other liquid organic media which function as diluents to partially replace more costly organic alcohols, as a means for facilitating removal of water, and as a means for reducing the polarity of the reaction mixture. Included within the scope of these other liquid organic media are: aldehydes, ketones, ethers, amines, amides, thiols and mixtures thereof.

The reaction mixture preferably is agitated during the heating.

Upon completion of the precursor forming reaction, the resulting catalyst precursor exists as a suspension of particles thereof in the reaction mixture. The reaction mixture is preferably cooled to between 20° and 50° C. and the catalyst precursor is then separated therefrom. This separation can be accomplished in a variety of ways. Generally, it takes place in two stages, namely, bulk separation and then final purification, e.g., by drying.

Bulk separation can be accomplished by filtering the reaction mixture to recover the catalyst precursor as a filter cake, by centrifuging the reaction mixture, and separating, e.g., by decanting, the supernatant liquid from the solid precursor, or by evaporating the liquid components of the reaction mixture to form a cake or paste of the catalyst precursor.

The precursor solids, after bulk separation, are then typically subjected to conditions sufficient to remove any residual liquid. This can be achieved by drying, a preferably continuous drying, to evaporate residual liquid media, by washing the precursor solids with water, or by employing both procedures. Before final purification is conducted, the separated catalyst precursor solids can be washed in the liquid organic media one or more times to remove any residual unreacted phophorus compound and/or any other organic soluble species followed by a repetition of bulk separation procedures.

Drying can be achieved by exposing the precursor to air at room temperature for a period of from about 1 to about 100 hours or by placing it in a forced hot air oven maintained at a temperature of less than about 180° C., typically between about 60° and about 150° C. for about 1 to about 5 hours. Alternatively, the precursor can be air dried at room temperature for between about 1 and about 48 hours then placed in the forced hot air oven. Drying of the catalyst precursor preferably should be conducted at temperatures below which crystal phase transitions occur and until a level of nearly constant weight is achieved. Drying under reduced pressure at room or elevated temperature, as described above, can also be employed as a suitable alternative.

II. ACTIVATION OF THE CATALYST PRECURSOR

The catalyst precursor must be activated in order to produce a final catalyst capable of exhibiting the improved yields illustrated herein. Activation, i.e., heating of the catalyst precursor in a selected atmosphere at a selected elevated temperature, can be accomplished in a separate step or in-situ in the reactor in which it will be used for the oxidation of hydrocarbons. Activation temperatures will vary slightly depending on whether the final catalyst will be employed for fixed bed or fluidized bed operations. Thus, for fixed or fluid bed operations, activation temperatures typically will vary from about 250° to about 450°, preferably from about 300° to about 410°, and most preferably from about 350° to about 410° C.

The atmosphere in contact with the catalyst precursor during activation will affect the performance of the catalyst. If activation is conducted for conventional periods in air alone, the catalyst performance will suffer significant reductions in yield.

Thus, it is critical to the process of the present invention that activation must be conducted in a gaseous atmosphere comprising air and a hydrocarbon and in the substantial absence of air alone.

More specifically, suitable activation atmospheres comprise and preferably consist essentially of a mixture, preferably a non-explosive mixture, of air and any hydrocarbon, preferably any hydrocarbon, described hereinafter which can be oxidized in accordance with the process of the present invention for using the catalyst.

Generally, the activation atmosphere will conveniently comprise a non-explosive mixture of air and the hydrocarbon to be oxidized by the catalyst.

Preferred hydrocarbons for use in activation include methane, butane, butene, butadiene and pentane.

The mole fraction of gaseous components in the activation atmosphere typically will be outside the explosive limits of the mixture.

Thus, when the activation atmosphere comprises air and butane, such mixtures preferably will contain, for example, between about 0.1 to about 1.8 (e.g., 1.0 to 1.2) mole % butane or above about 24 mole % butane.

Although not essential, it is desirable to maintain a steady flow of the activation atmosphere over the catalyst precursor surface during activation. Flow rates typically will be sufficient to provide a contact time with the catalyst of about 1 to about 10, preferably from about 1 to about 5, and most preferably from about 1 to about 3 seconds. Thus, suitable flow rates or space velocities of the activating atmosphere may be manipulated by one skilled in the art to achieve the desired contact time.

The period of activation will depend on the particular activation temperature and atmosphere selected as well as the contact time. Generally, such activation periods at the aforedescribed activation temperatures will typically vary from about 0.5 to about 72, preferably from about 1 to about 48, most preferably from about 1 to about 24 hours.

The preferred method of activation is to place the catalyst precursor in the reactor in which it will be employed and pass a gaseous mixture of air and butane in continuous flow over the catalyst precursor at temperatures of between about 390° and 410° C. until the conversion of the butane reaches about 90% on a molar basis. The temperature of the feed stream is then lowered to reaction temperature and product produced as desired. Thus, this activation procedure is simple and easy to achieve and actually produces collectible product during the course thereof.

III. CATALYST SHAPING

At some point in their preparation, the catalysts described herein preferably are formed into structures suitable for use in a reactor, although unshaped, powder catalyst can be employed. Techniques for forming the appropriate structures for use in a fixed bed reactor or a fluidized bed reactor are well known to those skilled in the art.

For example, the catalyst can be structured in unsupported form for use in fixed bed reactors by prilling or tableting, extruding, sizing and the like. Suitable binding and/or lubricating agents for pelleting or tableting include Sterotex ®, starch, calcium stearates, stearic acid, Carbowax, Methocel ®, Avicel ® and graphite and the like. Extrusion or pelleting of the catalyst can be achieved by forming a wet paste.

Supported catalysts for use in either fixed or fluidized bed operations employ carriers including alumina, silica, silica gel, silica-alumina, silicon carbide, ceramic donuts, magnesium oxide, titania and titaniasilica. Spray dried catalysts can also be employed for fluidized bed operations.

A catalyst support, if used, provides not only the required surface for the catalyst, but gives physical strength and stability to the catalyst material. The carrier or support typically possesses a surface area of from about 0.1 to about 200, preferably from about 1 to about 50, and most preferably from about 5 to about 30 m$^2$/g. A desirable form of carrier is one which has a rough enough surface to aid in retaining the catalyst adhered thereto during handling and under reaction conditions. The support may vary in size but generally is from about 2½ mesh to about 10 mesh in the Tyler Standard screen size. Alundum particles as large as ¼ inch are satisfactory. Supports much smaller than 10 to 12 mesh normally cause an undesirable pressure drop in the reactor, unless the catalysts are being used in a fluid bed apparatus.

The support material is not necessarily inert, that is, the particular support may cause an increase in the catalyst efficiency by its chemical or physical nature or both.

The amount of the catalyst deposited on the support is usually in the range of about 5 to about 90, preferably from about 5 to about 80% by weight based on the combined weight of catalyst and support. The amount of the catalyst deposited on the support should be enough to substantially coat the surface thereof and this normally is obtained with the ranges set forth above. With more absorbent carriers, larger amounts of material will be required to obtain essentially complete impregnation and coverage of the carrier. In a fixed bed process, the final particle size of the catalyst particles which are coated on a support will also preferably be about 2½ to about 10 mesh size. The supports may be of a variety of shapes, the preferred shape of the supports is in the shape of cylinders or spheres.

The particles size of a supported or unsupported catalyst used in fluidized beds is quite small, usually varying from about 10 to about 200 microns. Typically the attrition resistance of such catalysts is improved by the presence of zirconium or other modifier capable of hardening the catalyst. This can be achieved by the addition of oxides of the appropriate metal during preparation of the first catalyst precursor or during the water treatment step.

Inert diluents such as silica or $TiO_2$ may be present in the catalyst, but the combined weight of the essential active ingredients of vanadium, oxygen and phosphorus should preferably consist essentially of at least about 10, preferably at least about 30% by weight, based on the total weight of catalyst and support.

Shaping of unsupported catalyst can be conducted prior or subsequent to activation of the catalyst precursor. Preferably, shaping of the unsupported catalyst is conducted on the catalyst precursor prior to activation. The point during which shaping with supports or carriers is conducted will vary with the type of support.

Solid supports, such as silica alumina, can be added to the reaction mixture during the formation of the catalyst precursor.

IV. STABILITY ADDITIVES

In addition to vanadium, phosphorus, and oxygen, the catalyst of the present invention may also comprise effective amounts of stability additives which have been designated herein as promoters and/or activators. The typical additives which are used include magnesium, calcium, scandium, yttrium, lanthanum, uranium, cerium, chromium, manganese, iron, cobalt, nickel, copper, zinc, aluminum, gallium, indium, silicon, germanium, tin, bismuth, antimony, tellurium, lead, titanium, hafnium, lithium, potassium, cesium, zirconium, and mixtures thereof.

The promoters and/or activators are readily introduced into the catalyst during formation of the catalyst precursor by admixture with the vanadium and phosphorus compounds during the heating. These promoter and activator compounds, however, should be at least partially soluble in the solvent medium used in the particular preparation in order to be best suited for combination with the phosphorus and vanadium components of the catalyst. Typical compounds of titanium, which is the preferred activator, include titanium oxides, such as titanium oxide, titanium dioxide, titanium trioxide, titanium sesquioxide, titanium pentoxide, titanium halides such as titanium dichloride, titanium trichloride, titanium tetrachloride, titanium dibromide, titanium tribromide, titanium diiodide, titanium triiodide, titanium tetraiodide, and titanium tetrafluoride; titanium salts such as titanium phosphates and titanium sulfates; and organic titanium compounds, e.g., alkyl titanates such as methyl titanate, ethyl titanate, isopropyl titanate and butyl titanate and aryl titanates such as phenoxy titanium trichloride and phenyl titanate. Typical compounds of zinc (illustrative of activators as a class) are metallic zinc, zinc oxide, zinc chloride, zinc bromide, zinc iodide, zinc formate, zinc nitrate or zinc acetate.

V. CATALYST COMPOSITION

The P:V atomic ratio of the activated catalyst typically can vary from about 0.9:1 to about 1.6:1, preferably from about 1:1 to about 1.4:1, and most preferably from about 1:1 to about 1.2:1 (e.g. 1:1 to 1.13:1).

The average vanadium valence of the activated catalyst can vary typically from about 3.9 to about 4.7, preferably from about 3.9 to about 4.4, and most preferably from about 3.9 to about 4.2 (e.g. 4.0).

The surface area of the activated unsupported catalyst can vary typically from about 10 to about 100, preferably from about 10 to about 50, and most preferably from about 10 to about 40 $m^2/g$.

The above properties are determined by the following analytical methods.

The average vanadium valence is determined from magnetic susceptibility measurements performed from 77° to 300° K. using the Faraday technique. Contribution due to ferromagnetic impurities are removed prior to evaluation of the data. The measurements are carried out in an applied field of 6.35 kG. The average vanadium valence is determined from the Curie constant determined from plots of inverse susceptibility versus temperature, as are the Weiss temperatures, $\theta$.

Phosphorus to vanadium atomic ratio is determined by elemental analysis wherein vanadium is quantified by atomic absorption spectroscopy following acid digestion of the catalyst; quantification of phosphorus is conducted by gravimetric analysis using precipitation as the phosphomolybdate.

Surface area is determined by the BET method, the general procedures and theory for which are disclosed in H. Brunaur, P. Emmett, and E. Teller, J. of Am. Chem. Soc. Vol. 60, p. 309 (1938).

VI. VAPOR PHASE OXIDATION OF HYDROCARBONS

A. The catalysts of the present invention can be used to at least partially oxidize hydrocarbons to their corresponding carboxylic anhydrides. Such hydrocarbons which can be utilized in conjunction with the catalysts described herein comprise alkanes, typically alkanes of from 4 to about 10, preferably from about 4 to about 8, most preferably from about 4 to about 6 carbons; alkenes, typically alkenes of from about 4 to about 10, preferably from about 4 to about 8, most preferably from about 4 to about 6 carbons; cycloalkanes or cycloalkenes, typically cycloalkanes or cycloalkenes of from about 4 to about 14, preferably from about 6 to about 12, and most preferably from about 6 to about 10 carbons; alkyl substituted and unsubstituted aromatic compounds wherein the aryl portion thereof contains typically from about 6 to 14, preferably from about 6 to about 10 (e.g., 6) carbons and the alkyl portion contains typically from about 1 to about 10, preferably from about 1 to about 5 carbons, and mixtures thereof.

Representative examples of suitable alkanes include butane, pentane, isopentane, hexane, 3-methyl pentane, heptane, octane, isooctane, decane and mixtures thereof.

Representative examples of suitable alkenes include butene-1, butene-2 (cis or trans), 3-methylbutene-1, pentene-1, pentene-2, hexene-1, 3,3-dimethylbutene-1, 3-methylpentene-2, butadiene, pentadiene, cyclopentadiene, hexadiene, and mixtures thereof. It is also contemplated to use refinery streams rich in alkenes, particularly streams containing 70 percent of more butenes.

Representative examples of cycloalkanes, which can be methyl substituted, include cyclobutane, cyclopentane, methylcyclopentane, cyclohexane, methylcyclohexane, 1,4-dimethylcyclohexane, cycloheptane, and cyclooctane. Mixtures of hydrocarbons rich in alkanes and cycloalkanes having between 4 and 10 carbon atoms, i.e., containing about 70 weight percent or more alkanes and cycloalkanes can also be used.

Representative examples of suitable aromatic compounds include benzene, toluene, xylene, cumene, pseudocumene, durene and mixtures thereof.

Heterocyclic compounds such as furan, benzofuran, thiophene can be employed. Also suitable and readily available are naphthas obtained from paraffinic or naphthenic petroleum sources. Full boiling range naphthas (boiling within the range of about 35°–230° C.) can be used but it is preferred to use light naphtha cuts boiling within the range of about 35°–145° C. The naphthas usually contain about 5–15 percent benzene and alkylbenzenes. It will be understood that other mixtures can be used, such as a paraffinic raffinate from the glycol-water solvent extraction of reformates.

Thus, the catalyst of the present invention can be used to convert butane or butene to maleic anhydride; isopentane or isopentene to citraconic anhydride, maleic anhydride and α-carboxy maleic anhydride; pseudocumene to trimellitic anhydride; durene to pyromellitic anhydride; and o-xylene to phthalic anhydride.

A preferred hydrocarbon feed for the catalyst of the present invention for conversion to maleic anhydride is a n-C$_4$ hydrocarbon comprising a predominant amount of n-butane and more preferably at least 90 mol percent n-butane. In the following discussion and exemplification, therefore, butane is used in most examples to demonstrate (but not to limit) the use of the catalysts made by the process of this invention for producing maleic anhydride. It is contemplated that mixtures rich in butane can also be used, such as typical butane-butene refinery streams.

B. PREPARATION OF MALEIC ANHYDRIDE

The oxidation of n-butane to maleic anhydride may be accomplished by contacting n-butane, in low concentrations with oxygen in the presence of the described catalyst. Air is entirely satisfactory as a source of oxygen, but synthetic mixtures of oxygen and diluent gases, such as nitrogen, carbon dioxide and the like also may be employed. Air enriched with oxygen may be employed.

The gaseous feed stream to the oxidation reactors normally will contain air and typically from about 0.5 to about 10, preferably from about 1 to about 8, and most preferably from about 1.2 to about 5 mole % butane. About 1.0 to about 1.9 mole % of the butane in air is satisfactory for optimum yield of product for the process of this invention using a fixed bed reactor, and from about 2.5 to 4.0 mole % butane using a fluidized bed. Although higher concentrations may be employed, explosive hazards may be encountered. Lower concentrations of butane less than about 1%, of course, will reduce the production rate obtained at equivalent flow rates and thus are not normally economically employed.

Flow rates of the gaseous feed stream typically will be sufficient to provide a contact time with the catalyst of from about 0.5 to about 5, preferably from about 0.5 to about 3.5, most preferably from about 0.5 to about 2.5 seconds. At contact times of less than about 0.5 seconds, less efficient operations are obtained.

A variety of reactors will be found to be useful and multiple tube heat exchanger type reactors are quite satisfactory. The tubes of such reactors may vary in diameter typically from about ¾ inch to about 2 inches, and the length may be varied from about 3 to about 15 feet.

The oxidation reaction is an exothermic reaction and, therefore, relatively close control of the reaction temperature should be maintained. It is desirable to have the surface of the reactors at a relatively constant temperature and some medium to conduct heat from the reactors is necessary to aid temperature control. Various heat conductive materials may be employed, but it has been found that eutectic salt baths are completely satisfactory. One such salt bath is described below and is a eutectic constant temperature mixture. As will be recognized by one skilled in the art, the heat exchange medium may be kept at the proper temperature by heat exchangers and the like. The reactor or reaction tubes may be stainless steel, carbon-steel, nickel, glass tubes such as Vycor and the like. Both carbon-steel and nickel tubes have excellent long life under the conditions of the reactions described herein.

Optionally, the reactors contain a preheat zone of an inert material such as ¼ inch Alundum pellets, inert ceramic balls, metallic balls or chips and the like, present at about ½ to 1/10 the volume of the active catalyst present.

The temperature of reaction may be varied within some limits, but normally the reaction should be conducted at temperatures within a rather critical range. The oxidation reaction is exothermic and once reaction is underway, the main purpose of the salt bath or other media is to conduct heat away from the walls of the reactor and control the reaction. Better operations are normally obtained when the reaction temperature employed is no greater than about 100° C. above the salt bath temperature. The temperature in the reactor, of course, will also depend to some extent upon the size of the reactor and the butane concentration. Under usual operating conditions, in compliance with the preferred procedure of this invention, the average bed temperature referred to herein as the reaction temperature, measured by thermocouples disposed in the reactor, is typically from about 350° to about 450°, preferably from about 360° to about 420°, and most preferably from about 370° to about 410° C. Described another way, in terms of salt bath reactors with reactor tubes about 1.5 inches in diameter, the exit salt bath temperature will typically be controlled from about 330° to about 430°, preferably from about 340° to about 400°, and most preferably from about 350° to about 390° C. Under normal conditions, the temperature in the reactor ordinarily should not be allowed to go above about 450° C.

for extended lengths of time because of decreased yields and possible deactivation of the novel catalyst of this invention.

The reaction may be conducted at atmospheric, superatmospheric or below atmospheric pressure.

The maleic anhydride may be recovered by a number of ways well known to those skilled in the art. For example, the recovery may be by direct condensation or by absorption in suitable media, with subsequent separation and purification of the maleic anhydride.

While the above discussion is directed primarily to the use of a butane containing feed gas, it is equally applicable to the use of other hydrocarbon feed gases described herein subject to any modifications which would be obvious to one skilled in the art.

The following examples are given as specific illustrations of the claimed invention. It should be understood, however, that the invention is not limited to the specific details set forth in the examples. All parts and percentages in the examples as well as in the remainder of the specification are by weight unless otherwise specified.

In the following examples, the reactor used to test the catalyst is described as follows:

The reactor is U-shaped with one arm as the preheater (empty) and the other arm for packing catalyst. The reactor tube for the catalyst bed has a $\frac{3}{8}''$ O.D., 0.305" I.D., and 7 inches length, and is made of a stainless steel tube. Five cc of catalyst is charged to the reactor for testing and a 1/16 inch outer diameter thermocouple is placed 1 inch from the inlet of the catalyst bed to measure the reaction temperature. The reactor tube is immersed in a HITEC ® salt bath. Reactor inlet pressure is about 1 psig. Once a catalyst evaluation is started, the reaction is continued without interruption until the end of a series of runs. Recoveries are made at convenient time intervals. During a recovery, a scrubber with deionized water is placed in an ice-water bath and is connected to the reactor effluent to trap maleic anhydride and other condensable products. The scrubber effluent is connected to an on-line gas chromatograph for tail gas analysis. Maleic anhydride is titrated as maleic acid along with other acids using a potentiometer. Carbon balance is calculated according to the number of g-atoms of carbon in the reactor effluent to the g-atoms of carbon fed to the system.

Conversion of butane is calculated according to the following equation:

$$\% \text{ butane conversion} = \frac{\text{g moles of reacted butane}}{\text{g moles of butane fed}} \times 100$$

Maleic anhydride yield is calculated according to the following equation:

$$\% \text{ MA yield} = \frac{\text{g moles of maleic anhydride produced}}{\text{g moles of butane fed}} \times 100$$

The selectivity of maleic anhydride is calculated according to the following equation:

$$\% \text{ selectivity to } MA = \frac{\text{g moles of maleic anhydride produced}}{\text{g moles of butane reacted}} \times 100$$

Unless otherwise specified, all of the catalysts prepared in accordance with the following examples of the present invention possess a P:V atomic ratio of between 1:1 and 1.2:1, an average vanadium valence of 3.9 to 4.1, and a surface area of 5 to 15 m²/g. Furthermore, all preparations of the catalyst precursor are conducted using azeotropic distillation to remove water and other low boiling components formed in-situ.

COMPARATIVE EXAMPLE 1

This example illustrates the performance of a catalyst prepared generally in accordance with Katsumoto et al. U.S. Pat. No. 4,132,670.

Thus, a catalyst is prepared by the procedure of Example 1 of the above '670 patent as follows. A reflux flask is charged with 182 parts by weight $V_2O_5$ and 656 parts by weight of isobutanol (molar ratio isobutanol to $V_2O_5$ = 8.8:1). The contents are refluxed for 3 hours, removing water by azeotropic distillation. Then 277 parts by weight of 85% phosphoric acid is added slowly and the reaction temperature maintained at reflux for an additional 6 hours, removing water as formed. After standing at room temperature for 60 hours, the reaction mixture is heated at reflux for 7 hours removing water as formed. After standing for 20 hours at room temperature, the solvent is removed by distillation to form the slurry to leave 413 parts by weight of a blue solid which is ground to less than 20 mesh (Tyler series). To 150 parts by weight of this powder is added 35 parts by weight of water. The resulting paste is used to form tablets 2-3 mm in diameter (extrusion equipment being unavailable). The tablets are then dried in a forced hot air oven at about 150° C. for 2 hours. The dried tablets are then placed in the reactor and heated in a stream of air at 380° C. for 2 hours. The temperature of the air stream is slowly raised to 480° C. over 1 hour during which time 1.4 mole % n-butane is introduced into the air stream (contact time 2.4 sec.). Heating is continued at 480° C. for about 15 hours. The temperature of the reactor is then lowered to 442° C. and a sample of product analyzed after various on steam times. The results are summarized at Table 1.

EXAMPLE 1

Comparative Example 1 is repeated with the exception that the catalyst precursor is activated in a 1.2 mole % n-butane air stream mixture at 390° C. for 48 hours (contact time 2.5 sec.), i.e. Run 5. At this point the reaction temperature is controlled to be 390° C. and the reaction continued for total on stream time of 400 hours (contact time 2.5 sec.) removing samples for testing periodically. The results are summarized at Table 1.

From the data of Table 1 it can be seen that activation in a butane-air atmosphere improves the yield after about 200 hours on stream time, i.e. 46% (Comparative Example 1, Run 3) vs. 51% (Example 1, Run 7). More importantly, however, the yields of the catalyst of Example 1 are achieved at a reaction temperature of only 390° C. compared with 442° C. of Comparative Example 1. Consequently, the superior yields attained after 200 hours (Run 7) and thereafter represents a substantial increase in activity of the catalyst relative to the catalyst of the Comparative Example. Note also that even at the higher reaction temperatures, the yield of the catalyst activated in air drops significantly after about 200 hours and thereafter.

TABLE 1

| Run No. | | Activation Method* | Reaction Temp. °C. | Hours on Stream | Maleic Anhydride (M.A.) Yield % | Butane Conversion % | Selectivity % |
|---|---|---|---|---|---|---|---|
| Comparative | 1 | A | 442 | 75 | 41 | 96 | 43 |
| Example 1 | 2 | A | 442 | 162.5 | 52 | 98 | 53 |
| | 3 | A | 442 | 216 | 46 | 100 | 46 |
| | 4 | A | 442 | 384 | 41 | 100 | 41 |
| Example 1 | 5 | B | 390 | 50 | 31 | 52 | 60 |
| | 6 | B | 390 | 96 | 46 | 86 | 53 |
| | 7 | B | 390 | 192 | 51 | 88 | 58 |
| | 8 | B | 390 | 262.5 | 48 | 87 | 55 |
| | 9 | B | 390 | 400 | 49 | 78 | 63 |

*Activation Method A = air and then air + butane
Activation Method B = air + butane

COMPARATIVE EXAMPLE 2

The following comparative example illustrates the effect of activating by two different methods a V-P-O catalyst, prepared by a vanadium heterogeneous slurry vanadium reduction step in the presence of phosphoric acid (referred to herein as the simultaneous vanadium reduction-reaction method) in general accordance with the procedures of European Patent Application Publication No. 0039537.

Accordingly, to a 22 liter Morton TM kettle equipped with a heavy duty stirring shaft and paddle, thermometer and Dean-Stark TM trap with condenser is added 4 liters of isobutanol. $V_2O_5$ (1090.8 g) in powder form is then added to the kettle to obtain an orange slurry. Crystalline $H_3PO_4$ (1411.2 g), dissolved in isobutanol is added to the kettle in large increments as rapidly as possible to minimize exposure to air. Sufficient isobutanol is then added to bring the total isobutanol content in the kettle to 12 liters. The resulting reaction mixture is placed under a nitrogen atmosphere and heated, while stirring, to reflux temperature at about 104° C. The reaction mixture is allowed to reflux for 24 hours while removing 7 cc of water by the Dean-Stark TM trap. After the first 3 hours of refluxing, a turquoise color is obtained. The reaction mixture is then allowed to cool below 85° C. before the stirrer is turned off and the mixture allowed to settle for 18 hours. About 8 liters of isobutanol are siphoned off the top of the mixture into a suction filter. Stirring is then commenced and the remaining mixture is siphoned into the suction filter and allowed to filter for about 8 hours. The wet filter core is allowed to air dry under suction for about 48 hours, removed to drying trays and placed in a convection oven at 110° C. for 4 hours. About 67.93 g are removed and divided into two samples, i.e. samples A and B. Sample A is crushed and sieved to −10 +20 mesh Tyler series and 6 cc thereof placed in the reactor.

Sample A is contacted from the start with a 1.2% butane-air mixture at a 2 sec. contact time and samples of product are removed periodically after various hours on stream time as shown at Table 2, Runs 1 to 3.

Sample B, however, is calculated in air for 1 hour at 400° C., formed into 3/16″ tablets using 1.65 g steric acid and the tablets crushed and sized through −10 +20 mesh screen Tyler series. Sized Sample B is then placed into the reactor and a 1.2% butane-air mixture at 2 sec. contact time is passed through the reactor under conditions shown at Table 2, Runs 4–6 while periodically removing samples of product for analysis after the on stream times shown at Table 2, Runs 4–6.

TABLE 2

| Run No. | Activation Method* | Hours On Stream | Reaction Temp. °C. | Butane Conversion (%) | Selectivity To Maleic Anhydride (%) | Maleic Anhydride Yield (%) |
|---|---|---|---|---|---|---|
| 1 | butane-air | 70 | 400 | 93.5 | 44.7 | 41.8 |
| 2 | " | 80 | 395 | 80.8 | 54.5 | 44.0 |
| 3 | " | 123 | 393 | 78.0 | 56.6 | 44.2 |
| 4 | calcined in air | 72 | 400 | 100 | 56.6 | 56.5 |
| 5 | calcined in air | 82 | 395 | 96.9 | 59.8 | 57.9 |
| 6 | calcined in air | 121 | 393 | 91.0 | 60.8 | 55.3 |

As may be seen from the results of Table 2, catalysts prepared by a simultaneous vanadium reduction reaction procedure perform differently from those prepared by the separate vanadium reduction procedure of the present invention depending on the method of activation. More specifically, air calcination produces superior results when the catalyst is prepared by the simultaneous vanadium reduction-reaction procedure relative to in-situ activation using a butane-air mixture. Opposite results are obtained when the process of the present invention (separate vanadium reduction) is employed, namely, in-situ butane-air activation produces superior results.

Thus, Comparative Example 2 illustrates the criticality of the catalyst preparative procedure in selecting the appropriate activation method. Further evidence of this criticality is illustrated in U.S. patent application Ser. No. 326,343 filed Dec. 2, 1981 wherein a water treatment step is employed after forming a catalyst precursor by the simultaneous vanadium reduction-reaction method. The water treatment step disclosed in this application is believed to be responsible for superior performance of the water treated catalyst when activated in-situ in a butane-air mixture relative to conventional air calcination.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A process for oxidizing in the vapor phase at least one feed hydrocarbon to a carboxylic anhydride which comprises contacting the feed hydrocarbon, under conditions and in a manner sufficient to form at least one carboxylic anhydride, with a catalyst composition comprising vanadium, phosphorus, and oxygen, said catalyst composition being prepared by the process which comprises:
   (a) admixing to form a heterogeneous suspension at least one pentavalent vanadium compound with at least one organic alcohol in a manner and under conditions sufficient to condition said vanadium compound and reduce at least a portion of the pentavalent vanadium to a +4 valence state;
   (b) admixing at least one organic alcohol, said conditioned vanadium compound and at least one phosphorus containing compound, in a manner and under conditions sufficient to form a heterogeneous suspension of a vanadium-phosphorus-oxygen containing catalyst precursor composition having a vanadium valence of from about 3.9 to about 4.7, and a phosphorus to vanadium atomic ratio of from about 0.5:1 to about 2:1;
   (c) separating said catalyst precursor composition from said admixture; and
   (d) activating said catalyst precursor composition in the absence of air alone by contacting it with an atmosphere comprising a mixture of air and at least one hydrocarbon.

2. The process of claim 1 wherein the hydrocarbon feed is converted to a carboxylic anhydride selected from the group consisting of maleic anhydride, phthalic anhydride, trimellitic anhydride, pyromellitic anhydride, citraconic anhydride, and mixtures thereof.

3. The process of claim 1 wherein the hydrocarbon feed is selected from the group consisting of n-butane, butene, iso-pentane, orthoxylene, and mixtures thereof.

* * * * *